United States Patent
Lin et al.

(10) Patent No.: US 10,473,672 B2
(45) Date of Patent: Nov. 12, 2019

(54) METHODS FOR DIAGNOSING AND TREATING ALZHEIMERS DISEASE USING G72 PROTEIN AND SLC7A11 MRNA AS BIOMARKERS

(71) Applicant: Kaohsiung Chang Gung Memorial Hospital, Kaohsiung (TW)

(72) Inventors: Chieh-Hsin Lin, Pingtung (TW); Hsien-Yuan Lane, Taichung (TW)

(73) Assignees: KAOHSIUNG CHANG GUNG MEMORIAL HOSPITAL, Kaohsiung (TW); CHINA MEDICAL UNIVERSITY, Taichung (TW)

( * ) Notice: Subject to any disclaimer, the term of this patent is extended or adjusted under 35 U.S.C. 154(b) by 0 days.

(21) Appl. No.: 15/428,893

(22) Filed: Feb. 9, 2017

(65) Prior Publication Data
US 2018/0224468 A1    Aug. 9, 2018

(51) Int. Cl.
*G01N 33/68* (2006.01)
*C12Q 1/6883* (2018.01)

(52) U.S. Cl.
CPC ....... *G01N 33/6896* (2013.01); *C12Q 1/6883* (2013.01); *C12Q 2600/158* (2013.01); *C12Q 2600/16* (2013.01); *G01N 2333/70571* (2013.01); *G01N 2800/2821* (2013.01)

(58) Field of Classification Search
CPC ..... G01N 33/6896; G01N 2333/70571; G01N 2800/2821; C12Q 1/6883; C12Q 2600/158; C12Q 2600/16
See application file for complete search history.

(56) References Cited

U.S. PATENT DOCUMENTS

2014/0171413 A1* 6/2014 Lane .................. G01N 33/6896
514/211.13

OTHER PUBLICATIONS

Di Maria et al. Genetic variation in the G720/G30 gene locus (DAOA) influences the occurrence of psychotic symptoms in patients with Alzheimer's disease. J Alzheimers Dis. 2009;18(4):953-60. doi: 10.3233/JAD-2009-1194.*
Lin et al. Decreased mRNA expression for the two subunits of system xc(-), SLC3A2 and SLC7A11, in WBC in patients with schizophrenia: Evidence in support of the hypo-glutamatergic hypothesis of schizophrenia. J Psychiatr Res. Jan. 2016;72:58-63. doi: 10.1016/j.jpsychires.2015.10.007. Epub Oct. 22, 2015.*
Lopez et al. Effectiveness and safety of donepezil in Hispanic patients with Alzheimer's disease: a 12-week open-label study. J Natl Med Assoc. Nov. 2008;100(11):1350-8.*
Xu et al. Flexible combination of multiple diagnostic biomarkers to improve diagnostic accuracy. BMC Med Res Methodol. Oct. 31, 2015;15:94. doi: 10.1186/s12874-015-0085-z.*
McKhann, et al., "Clinical diagnosis of Alzheimer's disease: Report of the NINCDS-ADRDA Work Group* under the auspices of Department of Health and Human Services Task Force on Alzheimer's Disease", Neurology 34 (1984), pp. 939-944.
Lin, et al., "Distinctively higher plasma G72 protein levels in patients with schizophrenia than in healthy individuals", Molecular Psychiatry 19 (2014), pp. 636-637.

* cited by examiner

*Primary Examiner* — Gregory S Emch
(74) *Attorney, Agent, or Firm* — Hamre, Schumann, Mueller & Larson, P.C.

(57) ABSTRACT

A method for diagnosing Alzheimer's disease (AD) includes: obtaining a blood sample from a human subject suspected of having AD; determining a G72 protein level in the blood sample; determining an SLC7A11 mRNA expression level in the blood sample; comparing the G72 protein level with a first predetermined standard; comparing the SLC7A11 mRNA expression level with a second predetermined standard; and diagnosing the human subject with AD when the G72 protein level is higher than the first predetermined standard and the SLC7A11 mRNA expression level is higher than the second predetermined standard. An effective amount of a pharmaceutical composition may be administered to the diagnosed human subject for treating AD.

10 Claims, No Drawings
Specification includes a Sequence Listing.

```
                             SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: F1 primer for RT-qPCR of SLC7A11

<400> SEQUENCE: 1
ccatgaacgg tggtgtgtt                                              19

<210> SEQ ID NO 2
<211> LENGTH: 19
<212> TYPE: DNA
<213> ORGANISM: Artificial Sequence
<220> FEATURE:
<223> OTHER INFORMATION: R1 primer for RT-qPCR of SLC7A11

<400> SEQUENCE: 2
gaccctctcg agacgcaac                                              19

<210> SEQ ID NO 3
<211> LENGTH: 19
<212> TYPE: DNA
<213> ORGANISM: Artificial Sequence
<220> FEATURE:
<223> OTHER INFORMATION: F2 primer for RT-qPCR of GAPDH

<400> SEQUENCE: 3
ccactcctcc acctttgac                                              19

<210> SEQ ID NO 4
<211> LENGTH: 18
<212> TYPE: DNA
<213> ORGANISM: Artificial Sequence
<220> FEATURE:
<223> OTHER INFORMATION: R2 primer for RT-qPCR of GAPDH

<400> SEQUENCE: 4
accctgttgc tgtagcca                                               18

<210> SEQ ID NO 5
<211> LENGTH: 19
<212> TYPE: DNA
<213> ORGANISM: Artificial Sequence
<220> FEATURE:
<223> OTHER INFORMATION: F3 primer for RT-qPCR of GAPDH

<400> SEQUENCE: 5
agccacatcg ctcagacac                                              19

<210> SEQ ID NO 6
<211> LENGTH: 19
<212> TYPE: DNA
<213> ORGANISM: Artificial Sequence
<220> FEATURE:
<223> OTHER INFORMATION: R3 primer for RT-qPCR of GAPDH
```

```
<400> SEQUENCE: 6
gcccaatacg accaaatcc                                               19

<210> SEQ ID NO 7
<211> LENGTH: 19
<212> TYPE: DNA
<213> ORGANISM: Artificial Sequence
<220> FEATURE:
<223> OTHER INFORMATION: F4 primer for RT-qPCR of B2M

<400> SEQUENCE: 7
ttctggcctg gaggctatc                                               19

<210> SEQ ID NO 8
<211> LENGTH: 23
<212> TYPE: DNA
<213> ORGANISM: Artificial Sequence
<220> FEATURE:
<223> OTHER INFORMATION: R4 primer for RT-qPCR of B2M

<400> SEQUENCE: 8
tcaggaaatt tgactttcca ttc                                          23

<210> SEQ ID NO 9
<211> LENGTH: 20
<212> TYPE: DNA
<213> ORGANISM: Artificial Sequence
<220> FEATURE:
<223> OTHER INFORMATION: F5 primer for RT-qPCR of HPRT

<400> SEQUENCE: 9
acgtcttgct cgagatgtga                                              20

<210> SEQ ID NO 10
<211> LENGTH: 20
<212> TYPE: DNA
<213> ORGANISM: Artificial Sequence
<220> FEATURE:
<223> OTHER INFORMATION: R5 primer for RT-qPCR of HPRT

<400> SEQUENCE: 10
taatccagca ggtcagcaaa                                              20
```

METHODS FOR DIAGNOSING AND TREATING ALZHEIMERS DISEASE USING G72 PROTEIN AND SLC7A11 MRNA AS BIOMARKERS

FIELD

This disclosure relates to a method for diagnosing and treating Alzheimer's disease. Particularly, this disclosure relates to a method for diagnosing and treating Alzheimer's disease using two biomarkers, G72 protein and SLC7A11 mRNA.

BACKGROUND

The prevalence of dementia among the elderly population is increasing, and Alzheimer's disease (AD) is a neurodegenerative disease that is the most common cause of dementia. Early detection of AD is critical for the effectiveness of a subsequent treatment of the same disease. Alzheimer's disease is usually diagnosed based on the person's medical history, family medical history, and behavioral observations. The presence of characteristic neurological and neuropsychological features and the absence of alternative conditions are supportive in diagnosis. Advanced medical imaging with computed tomography (CT) or magnetic resonance imaging (MRI), and with single-photon emission computed tomography (SPECT) or positron emission tomography (PET) can be used to help exclude other cerebral pathology or subtypes of dementia.

Medical organizations have created diagnostic criteria to ease and standardize the diagnostic process for practicing physicians. For example, the National Institute of Neurological and Communicative Disorders and Stroke (NINCDS) and the Alzheimer's Disease and Related Disorders Association (ADRDA, now known as the Alzheimer's Association) established the most commonly used NINCDS-ADRDA criteria for diagnosis of AD (McKhann G. et al. (1984), *Neurology*, 34:939-944).

However, the aforesaid diagnosis methods are time-consuming and rely on the physicians' experience. Therefore, it is necessary to search for biomarkers that can give rise to a quick, reliable and accurate diagnosis of AD.

Currently, most studies of AD biomarkers have mainly focused on known pathological substrates for the disease, such as amyloid plaques and neurofibrillary tangles, which are respectively composed of the abnormally aggregated amyloid-β peptide (Aβ) and hyperphosphorylated Tau (pTau). Several studies have shown that the major species of amyloid-β peptide, i.e. a 42-amino acid peptide (Aβ1-42), is significantly decreased in the cerebrospinal fluid (CSF) of patients with AD, and that pTau is elevated in the CSF of patients with AD. Although the studies exploring use of these two biomarkers in the diagnosis of disease have been carried out, the results have not led to a useful, definitive method.

The N-methyl-D-aspartate receptor (NMDAR) is a glutamate receptor and ion channel protein found in nerve cells. The NMDAR is activated when glutamate and glycine (or D-serine) are bound thereto. The activated NMDAR allows positively charged ions to flow through the cell membrane thereof. The NMDAR is critical for synaptic plasticity, memory and cognitive function. Attenuation of NMDAR-mediated neurotransmission results in loss of neuronal plasticity and cognitive deficits in the aging brain, which might account for clinical deterioration and brain atrophy.

There are several avenues to enhance NMDAR activation, and one of them is through inhibition of D-amino acid oxidase (DAAO), which is a flavoenzyme of peroxisomal enzyme responsible for degrading D-serine and D-alanine. The inhibition of DAAO thereby raises the level of D-amino acids which are neurotransmitters for the coagonist site of the NMDAR. The gene encoding D-amino acid oxidase activator (DAOA, also known as G72) is primate specific and is located on chromosome 13q32-q34. G72 protein may play an important role in the modulation of NMDA signaling. In a previous study, C. H. Lin et al. found that the peripheral G72 protein expression is distinctively higher in patients with schizophrenia than in healthy individuals, indicating that the peripheral expression of G72 protein may have the potential to be a diagnostic biomarker for schizophrenia (C. H. Lin et al. (2014), *Molecular Psychiatry*, 19:1-2).

The cystine/glutamate antiporter system $x_c^-$ is a sodium-independent acidic amino acid transporter which mediates the uptake of cystine into cells in exchange for glutamate in a 1:1 ratio. System $x_c^-$ is composed of a heavy chain subunit (4F2hc, SLC3A2) and a light chain subunit (xCT, SLC7A11). Cystine is reduced to cysteine intracellularly after being taken up by system $x_c^-$. Cysteine is the rate-limiting substrate for the synthesis of antioxidant glutathione (GSH) which is one of the most important antioxidants in the brain. System $x_c^-$ also plays a critical role in the release of glutamate which is the most abundant amino acid neurotransmitter in the mammalian brain.

As far as the applicants are aware, the correlation of either G72 protein or System $x_c^-$ with AD has yet to be understood. In order to explore a new biomarker for diagnosing AD, the applicants have conducted experiments and statistical analyses to determine the diagnostic accuracy of G72 protein and/or SLC7A11 mRNA in detection of AD. The applicants surprisingly found from experiments that even though G72 protein or SLC7A11 mRNA alone may be useful as a potential biomarker for the detection of AD, the combination of G72 protein and SLC7A11 mRNA can lead to an even more reliable diagnosis of AD.

SUMMARY

According to one aspect of the present disclosure, a method for diagnosing Alzheimer's disease (AD) includes: obtaining a blood sample from a human subject suspected of having AD; determining a G72 protein level in the blood sample; determining an SLC7A11 mRNA expression level in the blood sample; comparing the G72 protein level with a first predetermined standard; comparing the SLC7A11 mRNA expression level with a second predetermined standard; and diagnosing the human subject with AD when the G72 protein level is higher than the first predetermined standard and the SLC7A11 mRNA expression level is higher than the second predetermined standard.

According to another aspect of the present disclosure, a method for diagnosing and treating AD includes: obtaining a blood sample from a human subject suspected of having AD; determining a G72 protein level in the blood sample; determining an SLC7A11 mRNA expression level in the blood sample; comparing the G72 protein level with a first predetermined standard; comparing the SLC7A11 mRNA expression level with a second predetermined standard; diagnosing the human subject with AD when the G72 protein level is higher than the first predetermined standard and the SLC7A11 mRNA expression level is higher than the second predetermined standard; and administering to the diagnosed human subject an effective amount of a pharmaceutical composition for treating AD.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

As used herein, the term "Alzheimer's disease" (AD) refers to a progressive mental deterioration manifested by memory loss, confusion and disorientation beginning in late midlife and typically resulting in death in five to ten years. Pathologically, AD can be characterized by thickening, conglutination, and distortion of the intracellular neurofibrils, neurofibrillary tangles and senile plaques composed of granular or filamentous argentophilic masses with an amyloid core.

As used herein, the terms "diagnose", "diagnosis" or "diagnosing" refer to distinguishing or identifying a disease, syndrome or condition or distinguishing or identifying a person having a particular disease, syndrome or condition. In illustrative embodiments of the present disclosure, assays and algorithms are used to diagnose AD in a subject based on an analysis of a sample.

The term "treat", "treating" or "treatment" as used herein, means decrease, suppress, attenuate, diminish, arrest, or stabilize the development or progression of a disease (e.g., a disease or disorder delineated herein), lessen the severity of the disease or improve the symptoms associated with the disease.

In an attempt to identify new biomarkers for AD, the applicants compared the G72 protein level and/or SLC7A11 mRNA expression level of the blood sample between the healthy subjects and the subjects identified as patients having AD. The applicants' study revealed that both the G72 protein level and SLC7A11 mRNA expression level were differentially expressed between the subjects in the AD and control groups, suggesting that the G72 protein or SLC7A11 mRNA can serve as a biomarker for the detection of AD. However, based on the receiver operating characteristics (ROC) curve analysis, the sensitivity for the G72 protein and the specificity for the SLC7A11 mRNA are only modest. To the applicants' surprise, the combination of the G72 protein level and the SLC7A11 mRNA expression level provide for a better diagnostic ability to differentiate between the subjects in the AD and control groups, and thus can lead to an even more reliable diagnosis of AD.

Accordingly, the present disclosure provides a method for diagnosing Alzheimer's disease (AD), which includes:
  obtaining a blood sample from a human subject suspected of having AD;
  determining a G72 protein level in the blood sample;
  determining an SLC7A11 mRNA expression level in the blood sample;
  comparing the G72 protein level with a first predetermined standard;
  comparing the SLC7A11 mRNA expression level with a second predetermined standard, and
  diagnosing the human subject with AD when the G72 protein level is higher than the first predetermined standard and the SLC7A11 mRNA level is higher than the second predetermined standard.

According to the present disclosure, the blood sample can be obtained anytime from the human subject, and may be a fasting or non-fasting blood sample. In one embodiment of the present disclosure, the blood sample is obtained in the morning. In another embodiment of the present disclosure, the blood sample is a fasting blood sample obtained between the hours of 7 AM and 9 AM.

The aforementioned method may further include a blood separation step. The blood separation step may be conducted to separate plasma or serum from the blood sample so as to determine the G72 protein level. Furthermore, the blood separation step may be conducted to separate white blood cells from the blood sample so as to determine the SLC7A11 mRNA expression level.

According to the present disclosure, the G72 protein level and the SLC7A11 mRNA expression level can be determined by any means that is known to those skilled in the art.

In certain embodiments, the G72 protein level can be determined by immunoassays. Exemplary immunoassays may include Western blot immunoassay, multiplex immunoassay, enzyme linked immunosorbent assay (ELISA), radioimmunoassay (RIA), immunoradiometric assay (IRMA), fluorescent immunoassay (FIA), chemiluminescent immunoassay and immunonephelometry.

The G72 protein level may be determined using an antibody-based binding moiety which specifically binds to G72 protein. In an embodiment of this disclosure, the antibody-based binding moiety is an antibody.

"Antibody-based binding moiety" or "antibody" includes immunoglobulin molecules and immunologically active determinants of immunoglobulin molecules, e.g., molecules that contain an antigen-binding site that specifically binds to G72 protein. The term "antibody-based binding moiety" is intended to include whole antibodies of any isotype (e.g., IgG, IgA, IgM, IgE, etc.), and fragments thereof that are also specifically reactive with G72 protein.

In this disclosure, the antibody-based binding moiety may include polyclonal, monoclonal or other purified preparations of antibodies and recombinant antibodies, and is further intended to include humanized antibodies, bi-specific antibodies, and chimeric molecules having at least one antigen-binding determinant derived from an antibody molecule.

In this disclosure, "antibody-based binding moiety" or "antibody" may include a capture antibody and a detecting antibody.

The term "capture antibody" as used herein is defined as an antibody, whether monoclonal, polyclonal or of an immunoreactive fragment, which is capable of binding to an antigen of interest, and thereby allows the recognition of the antigen by a subsequently applied antibody. The capture antibody can be used in either a heterogeneous (solid phase) or homogeneous (solution phase) assay. The capture antibody may be immobilized onto a solid phase.

The term "detecting antibody" as used herein is defined as an antibody having a detectable label that is specific for (i.e., binds, is bound by, or forms a complex with) one or more analytes of interest in a sample. The term also encompasses an antibody that is specific for one or more analytes of interest, wherein the antibody can be bound by another species that includes a detectable label. Examples of detectable labels include, but are not limited to, a radioactive label, a hapten label, a fluorescent label, a chemiluminescent label, an enzymatic label, a nucleotide (e.g., oligonucleotide) label, an epitope tag, and combinations thereof.

Examples of hapten labels may include biotin/streptavidin and digoxigenin.

Examples of epitope tags may include T7, c-Myc, HA, VSV-G, HSV, FLAG, V5 and HIS.

Antibodies can be fragmented using conventional techniques. The term "fragment(s) thereof" refers to segments of proteolytically-cleaved or recombinantly-prepared portions of an antibody molecule that are capable of selectively reacting with a certain protein.

Non-limiting examples of proteolytically-cleaved fragments and/or recombinantly-prepared portions include Fab, F(ab')2, Fab', Fv, dabs and a single-chain variable fragment (scFv) containing a VL and VH domain joined by a peptide linker. The scFv's may be covalently or non-covalently linked to form antibodies having two or more binding sites.

According to the present disclosure, the G72 protein level is positively correlated to the intensity of the signal emitted from the detectably labeled antibody.

In one exemplary embodiment of the present disclosure, the antibody-based binding moiety is detectably labeled by linking the antibody to an enzyme. The enzyme, in turn, when exposed to its substrate, will react with the substrate in such a manner as to produce a chemical moiety which can be detected, for example, by spectrophotometric, fluorometric or visual means. The enzymes which can be used to react with the detectable label of the antibodies of the present disclosure include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase (HRP), alkaline phosphatase, asparaginase, glucose oxidase, β-galactosidase, ribonuclease, urease, catalase, glucose-VI-phosphate dehydrogenase, glucoamylase and acetylcholinesterase.

In certain embodiments, the antibody may also be labeled with a fluorescent compound. When the fluorescently labeled antibody is exposed to light of the proper wavelength, its presence can be detected due to fluorescence. Fluorescent compounds suitable for the present disclosure include, but are not limited to, CYE dyes, fluorescein isothiocyanate (FITC), rhodamine, phycoerythrin, coriphosphine-O (CPO), phycocyanin (PE), allophycocyanin (APC), o-phthaldehyde, fluorescamine and tandem dyes.

Examples of tandem dyes include PE-Cy5 (PC5), PE-Cy7 (PC7) and PE-Texas Red.

In certain embodiments, the antibody may be detected by fluorescence emitting metals, such as $^{152}$Eu or other lanthanide series metals. These metals can be attached to the antibody by means of a metal-chelating group such as diethylenetriaminepentaacetic acid (DTPA) or ethylenediaminetetraacetic acid (EDTA).

In certain embodiments, the antibody may be detected by coupling to a chemiluminescent. The presence of the chemiluminescent-antibody is then determined by detecting the presence of luminescence that arises during the course of a chemical reaction. Examples of chemiluminescent compounds include, but are not limited to, luminol, luciferin, isoluminol, theromatic acridinium ester, imidazole, acridinium salt and oxalate ester.

Detection may also be accomplished using any of a variety of other immunoassays. For example, by radioactively labeling an antibody, it is possible to detect the antibody through the use of radioimmunoassays. Means of detecting radioactive isotopes include, but are not limited to, gamma counter, scintillation counter and autoradiography. The antibody can be detected by radioactive isotopes. Examples of radioactive isotopes include, but are not limited to, $^{3}$H, $^{31}$P, $^{35}$S, $^{14}$C, and $^{125}$I.

According to the present disclosure, the SLC7A11 mRNA expression level may be determined using at least one of the following methodologies: polymerase chain reaction, real time polymerase chain reaction (q-PCR), reverse transcription polymerase chain reaction (RT-PCR), quantitative RT-PCR (RT-qPCR), hybridization, probe hybridization and gene expression array. In one embodiment of the present disclosure, the SLC7A11 mRNA expression level is determined using quantitative RT-PCR.

According to the present disclosure, the term "predetermined standard" may indicate a range, a value or a cutoff value for a G72 protein level or an SLC7A11 mRNA expression level in a blood sample of a healthy individual, which is determined by selected means. The cutoff value between a population of healthy individuals and subjects that have AD can be determined by those skilled in the art.

The term "healthy individual" refers to an individual not having any symptoms associated with AD or not at risk of developing AD, i.e. an individual considered healthy after evaluation by a professional medical practitioner.

In order to assess the progression of AD or the effectiveness of a treatment for AD, a G72 protein level and an SLC7A11 mRNA expression level as detected in a previous examination may also be used as a reference for the human subject.

In one embodiment of the present disclosure, the first and second predetermined standards for the G72 protein level and the SLC7A11 mRNA expression level in the human subject suspected of having AD are respectively determined by Western blot immunoassay and RT-qPCR, giving a standard value of 2.3285 ng/mL and a standard delta CT value of 12.185 (calculated by subtracting the average CT value of the selected housekeeping genes from the CT value of SLC7A11) as the cutoff values for a G72 protein level and an SLC7A11 mRNA expression level.

According to the present disclosure, the presence of AD may also be determined based on a combined cut-off value of the determined G72 protein level and the determined SLC7A11 mRNA expression level. In certain embodiments, the combined cut-off value may be calculated by an equation formulated using statistical analysis (such as discriminant function analysis, logistic regression analysis, receiver operating characteristic curve analysis and ridge regression analysis).

According to the present disclosure, if the human subject is diagnosed with AD, the following treatment step may be used in combination with the steps in the aforesaid diagnostic method: administering to the diagnosed human subject an effective amount of a pharmaceutical composition for treating AD. Therefore, the present disclosure also provides a method for diagnosing and treating AD.

According to the present disclosure, the pharmaceutical composition for treating AD may contain an active ingredient well-known in the art, and hence is only briefly described herein.

In certain embodiments, the active ingredient used in the the pharmaceutical composition for treating AD is selected from the group consisting of N-methyl-D-aspartate receptor receptor (NMDAR) antagonists, cholinesterase modulators (such as acetylcholineesterase inhibitors (AChEIs), acetylcholine synthesis modulators, acetylcholine storage modulators, acetylcholine release modulators, etc.), Aβ inhibitors (such as Aβ plaque removal agents, inhibitors of Aβ plaque formation, inhibitors of amyloid precursor protein processing enzymes, β-amyloid converting enzyme inhibitors, β-secretase inhibitors, and γ-secretase modulators), nerve growth factor agonists, hormone receptor blockade agents, neurotransmission modulators, and combinations thereof.

Suitable NMDAR antagonists include, but are not limited to, memantine, rimantadine, and amantadine.

Suitable cholinesterase modulators may be AchEIs which include, but are not limited to, donepezil, rivastigmine, galantamine, tacrine, metrifonate, huperzine-A, physostigmine, neostigmine, icopezil, and zanapezil.

Suitable Aβ inhibitors include, but are not limited to, tarenflurbil, tramiprosate, clioquinol, PBT-2 and other 8-hydroxyquinilone derivatives, Aβ plaque removal agents, inhibitors of AR plaque formation, inhibitors of amyloid precursor protein processing enzymes, β-amyloid converting enzyme inhibitors, β-secretase inhibitors, and γ-secretase modulators.

Suitable nerve growth factor agonists include, but not limited to, xaliproden, a brain derived neurotrophic factor, and a nerve growth factor.

Suitable hormone receptor blockade agents include, but are not limited to, leuproelide and a derivative thereof.

Suitable neurotransmission modulators include, but are not limited to, ispronicline.

EXAMPLES

The present disclosure will be described in more detail with reference to the following examples, which are given for the purpose of illustration only and are not intended to limit the scope of the present disclosure.

The experiments below were conducted using a protocol approved by the Institutional Review Board (IRB) in accordance with the current revision of the Declaration of Helsinki. After complete description of the experiments to the participants, written informed consent was obtained in line with IRB guidelines.

239 human subjects participated. It should be noted that each of the participants had no history of significant cerebrovascular disease, a Hachinski Ischemic Score not greater than 4, and no major neurological, psychiatric or medical conditions other than AD. Moreover, each of the participants had no substance (including alcohol) abuse or dependence, no symptoms of delusion, hallucination or delirium, no severe visual or hearing loss, and was able to follow the protocol. In addition, to exclude potential confounding effects, it was ascertained that each of the participants was a non-smoker and had no DSM-IV diagnosis of substance (including alcohol) abuse.

Among all the 239 participants, 130 human subjects were identified as healthy volunteers, and are hereinafter referred to as the "control group". These subjects were aged ≥18 years, were free of any Axis I or II psychiatric disorders, were physically and neurologically healthy, and had laboratory assessments (including urine/blood routine, biochemical tests, and electrocardiography) within normal limits. The remaining 109 human subjects were identified as patients having AD, and are hereinafter referred to as the "AD group". These patients with AD (1) satisfied the criteria for probable AD as proposed by the National Institute of Neurological and Communicative Disorders and Stroke and the Alzheimer's Disease and Related Disorders Association (NINCDS-ADRDA) and had a Clinical Dementia Rating (CDR) score of 1 or greater, and (2) were physically healthy and had laboratory assessments (including urine/blood routine, biochemical tests, and electrocardiography) within normal limits.

Out of the 130 control group subjects and 109 AD group subjects, 40 individuals from the control group and 70 patients from the AD group were selected and matched by age for further analysis. Table 1 shows the clinical characteristics (i.e. sex, age, and CDR score) of all the subjects ("age-unmatched"), as well as the subset of the subjects matched by age ("age-matched"). Since results were found to be similar irrespective of whether matching or not matching was applied, only the subset of subjects matched by age will be discussed in this example.

TABLE 1

| Demographic Characteristics of Subjects | | | | |
|---|---|---|---|---|
| | Age-unmatched | | Age-matched | |
| | Control Group | AD Group | Control Group | AD Group |
| # Subjects | 130 | 109 | 40 | 70 |
| Age [a] | 43.1 ± 18.2 | 74.6 ± 7.9 | 65.9 ± 13.0 | 70.1 ± 6.1 |
| (Range) | (19-88) | (50-89) | (45-88) | (50-78) |
| Sex (F/M) | 63/67 | 71/38 | 17/23 | 47/23 |
| CDR score [a] | 0 | 1.3 ± 0.6 | 0 | 1.2 ± 0.5 |

[a] shown as mean ± standard deviation

Example 1. Analysis of G72 Protein Level and SLC7A11 mRNA Expression Level for Diagnosis of AD <Determination of G72 Protein Level in Plasma>

Blood sampling was performed between the hours of 7 am and 9 am after all the subjects had fasted for more than 8 hours.

10 ml of peripheral venous blood was collected from each of the subjects in the control and AD groups into an EDTA-containing blood collection tube by personnel trained in phlebotomy using sterile technique. The tube was centrifuged at 1500×g for 10 minutes at 4° C. The plasma thus obtained was quickly transferred into a different tube and immediately stored at −80° C. until further analysis.

The G72 protein level in the plasma was determined with Western blot analysis. 100 µl of the plasma sample was processed by using ProteoPrep® Blue Albumin and IgG Depletion Kit (Sigma) to deplete the high abundant proteins in the plasma. The low-abundance protein fractions were collected and were each concentrated to 100 µl. Then, 10 µl of the respective concentrated fraction was mixed with a 4-fold amount of a sample buffer (containing 500 mM Tris-HCl (pH 6.8), 16% SDS, 80% glycerol, 400 mM DTT, and 0.08% bromophenol blue). Protein separation was conducted on 12% SDS-PAGE. The separated proteins in the gel were transferred to a 0.45 µm polyvinylidene difluoride (PVDF) membrane (Millipore). The blotted PVDF membrane thus obtained was subjected to a blocking treatment by virtue of 5% nonfat dry milk in TBST (containing 20 mM Tris-HCl (pH 7.6), 500 mM sodium chloride, and 0.1% Tween 20) for 1 hour at room temperature, and was then incubated with a goat anti-G72 antibody (G72(N15):sc-46118, Santa Cruz Biotechnology) diluted 1:1000 in TBST overnight at 4° C. The membrane was washed 3 times (15 minutes each time) in TBST and was incubated for 2 hours with an HRP-linked anti-goat IgG secondary antibody (sc- 2030, Santa Cruz Biotechnology) diluted 1:5000 in TBST. After another 3 washes in TBST, the blot was visualized with an ECL Advance Western Blotting Detection Kit (RPN2135, GE Healthcare). The stained membrane was then photographed on ImageQuant LAS 4000 mini (GE Healthcare), and was quantified using ImageQuant™ TL 7.0 software (GE Healthcare) by measuring the relative intensity from each band and conducting normalization to the G72 recombinant protein (20 or 50 ng, kindly donated by Dr. Hao-Teng Chang from China Medical University Hospital, Taichung, Taiwan) signals. The Western blot analysis was repeated twice.

<Determination of SLC7A11 mRNA Expression Level in White Blood Cells (WBC)>

10 ml of peripheral venous blood was collected from each of the subjects in the control and AD groups into an EDTA-containing blood collection tube by personnel trained in phlebotomy using sterile technique. The tube was centrifuged at 1500×g for 10 minutes at 4° C. Red blood cells (RBC) were lysed by adding 1×RBC lysis buffer (Genepure Technology Co.) to the tube, and then WBC were obtained after centrifugation at 1500×g for 10 minutes.

To investigate the gene expression of a light chain subunit of system $x_c^-$ in WBC, the mRNA expression level of SLC7A11 in WBC was examined with quantitative real-time PCR.

RNA was isolated from the WBC obtained above using TRI Reagent (Molecular Research Center, Inc.) according to the protocol provided by the manufacturer. The RNA sample thus prepared was treated with DNase I to avoid DNA contamination. RNA concentration was determined by absorbance at 260 nm using an ND-1000 UV-Vis spectrophotometer (Thermo Fisher Scientific Inc.), followed by storage at −80° C.

First-strand cDNA was then synthesized by the following steps. A 2.5 µg aliquot of the isolated RNA was incubated with 0.5 µg of a random hexamer and oligo-dT primers at 70° C. for 5 minutes to briefly denature the RNA secondary structure, followed by rapid cooling on ice to facilitate the annealing process between the primer and the RNA. 1500 uM dNTP, 20 U RNase inhibitor, 200 U MMLV reverse transcriptase (Promega), and a reverse transcription buffer were added to the PCR tube containing the RNA and primers, for a final volume of 20 µl. The PCR tube was then incubated at 37° C. for 90 minutes for extension, followed by heating at 70 for 10 minutes so as to inactivate the reverse transcriptase. Synthesized first-strand cDNA was thus obtained.

After cDNA synthesis, SYBR Green Master Mix on Real-Time PCR Detection System was employed to measure the mRNA expression of SLC7A11.

Specifically, 2 µl of the synthesized cDNA sample (250 ng), 10 µl of Master mix (Roche), and each primer at a concentration of 600 nM (the primer pair for amplifying SLC7A11 is listed in Table 2) were added in a PCR tube, for a total of 20 µl reaction volume. The sample in the PCR tube was pre-incubated at 95° C. for 10 minutes during the denaturation process to activate the Hot-Start DNA polymerase, followed by primer annealing at 58° C. for 45 seconds and DNA elongation for 45 cycles at 95° C. for 15 seconds. A melting curve program was run to verify the PCR product specificity. The RT-qPCR reaction was carried out twice. Negative controls were included to confirm that the sample was not cross-contaminated.

Three housekeeping genes were used as endogenous controls, including the genes of glyceradehyde-3-photosphate dehydrogenase (GAPDH) (for which two primer pairs were used), beta-2-microglobulin (B2M), and hypoxanthine phosphoribosyltransferase (HPRT). The primer pairs of these housekeeping genes used in RT-qPCR are shown in Table 2. The average of the CT values of these housekeeping genes was used in the calculation of the relative mRNA expression level of SLC7A11 in the sample ($\Delta CT = C_{T,\ target} - C_{T,\ housekeeping}$).

TABLE 2

Primer Pairs Used in RT-qPCR

| Target Gene Name | Primer | The corresponding nucleotide residues in the target Gene/ Sequence (5'-3') | PCR Product Size (bp) |
|---|---|---|---|
| SLC7A11 (corresponding to NCBI accession no. NM_014331.3) | F1 | 1269-1287 ccatgaacggtggtgtgtt (SEQ ID NO: 1) | 60 |
| | R1 | 1328-1310 gaccctctcgagacgcaac (SEQ ID NO: 2) | |
| GAPDH (corresponding to NCBI accession no. NM_002046.5) | F2 | 1058-1076 ccactcctccaccttttgac (SEQ ID NO: 3) | 102 |
| | R2 | 1159-1142 accctgttgctgtagcca (SEQ ID NO: 4) | |
| GAPDH (corresponding to NCBI accession no. NM_002046.5) | F3 | 169-187 agccacatcgctcagacac (SEQ ID NO: 5) | 66 |
| | R3 | 234-216 gcccaatacgaccaaatcc (SEQ ID NO: 6) | |
| B2M (corresponding to NCBI accession no. NM_004048.2) | F4 | 105-123 ttctggcctggaggctatc (SEQ ID NO: 7) | 86 |
| | R4 | 190-168 tcaggaaatttgactttccattc (SEQ ID NO: 8) | |
| HPRT (corresponding to NCBI accession no. NM_000194.2 | F5 | 308-327 acgtcttgctcgagatgtga (SEQ ID NO: 9) | 102 |
| | R5 | 409-390 taatccagcaggtcagcaaa (SEQ ID NO: 10) | |

<Statistical Analysis of G72 Protein Level and SLC7A11 mRNA Expression Level>

Baseline characteristics were calculated for the AD and control groups. Numeric data are presented as means±standard deviation (SD). P-value between the AD and control groups was calculated based on t-test, and a probability value less than 0.05 (p<0.05) was considered to indicate statistical significance.

A receiver operating characteristics (ROC) analysis for G72 Protein, SLC7A11 mRNA and the combination thereof was applied by plotting the proportion of true-positive results (sensitivity) vs. the proportion of false-positive results (1−specificity).

An equation (I) for the weighted value of G72 protein level and SLC7A11 mRNA expression level in combination as shown below was formulated using the logistic regression model, with G72 protein level and SLC7A11 mRNA expression level as the covariates:

$$A = -13.246 + B \times 3.197 + C \times 2.273 \qquad (I)$$

A=Weighted value
B=G72 protein level (ng/µL)
C=ΔCT value

An area under the ROC curve (AUC) for each biomarker was also calculated and used as an index to determine which biomarker had a good diagnostic ability to distinguish patients from healthy subjects (see Zweig M. H. (1993), *Clin. Chem.*, 39:561-577). Interpretations of AUC value include: outstanding (AUC>0.9), excellent (AUC=0.8~0.9), acceptable (AUC=0.7~0.8), poor (AUC=0.6~0.7), and no discrimination (AUC=0.5).

Results:

G72 Protein as a Biomarker for Diagnosing AD

As shown in Table 3, regarding the matched cohort, the expression level of G72 protein in the plasma of the AD group was markedly higher than that of the control group. Specifically, the expression levels of G72 protein in the matched AD group and control group were 2.63±1.20 ng/μL and 1.72±0.71 ng/μL, respectively. These results indicate that the G72 protein in a plasma sample can serve as a biomarker for the detection of AD.

As shown in Table 4, the ROC analysis of the G72 expression level for the AD group vs. control group indicated an optimal cutoff value of 2.3285 ng/μL, suggesting that a G72 protein level in plasma which is equal to or greater than 2.3285 ng/μL may be indicative of AD. Findings also showed that the ROC curve analysis of G72 expression levels for the AD group vs. control group had good specificity (0.900) but only modest sensitivity (0.543). Thus, a diagnostic method with higher levels of sensitivity may be warranted.

In addition, the AUC for G72 protein levels in plasma is 0.726, suggesting an acceptable diagnostic ability to distinguish the subjects in the control group from those in the AD group.

Overall, these results indicate that using the G72 protein in plasma as the sole biomarker for AD is considered to provide an acceptable diagnostic ability to distinguish subjects in the control group from those in the AD group. Moreover, a diagnostic method with higher levels of sensitivity may be warranted.

SLC7A11 mRNA as a Biomarker for Diagnosing AD

The $\Delta$CT value indicative of the SLC7A11 mRNA expression level in WBC of the AD group was markedly higher than that of the control group (see Table 3). Specifically, the $\Delta$CT values indicative of the expression levels of SLC7A11 mRNA in the matched AD group and control group were 13.82±1.29 and 12.44±1.37, respectively. These results indicate that the SLC7A11 mRNA in WBC samples can serve as a biomarker for the detection of AD.

Referring to Table 4, the ROC analysis of the $\Delta$CT values of SLC7A11 mRNA expression levels for the AD group vs. control group indicated an optimal cutoff value of 12.185, suggesting that a $\Delta$CT value of SLC7A11 mRNA expression level in WBC which is equal to or greater than 12.185 may be indicative of AD. Findings also showed that the ROC curve analysis of $\Delta$CT values indicative of SLC7A11 mRNA expression levels for the AD group vs. control group had good sensitivity (0.929) but only modest specificity (0.45). Thus, a diagnostic method with higher levels of specificity may be warranted.

As shown in Table 4, the AUC for SLC7A11 mRNA expression levels in WBC is 0.764, suggesting an acceptable diagnostic ability to distinguish the subjects in the control group from those in the AD group.

Overall, similar to using only the G72 protein in plasma as the sole biomarker for AD, using the SLC7A11 mRNA in WBC as the sole biomarker for AD is also considered to provide an acceptable diagnostic ability to distinguish the subjects in the control group from those in the AD group. A diagnostic method with higher levels of specificity may be warranted.

Combination of G72 Protein Level in Plasma and SLC7A11 mRNA Expression Level in WBC for Diagnosing AD Overall, the G72 protein level and the $\Delta$CT value indicative of SLC7A11 mRNA expression level of the AD group were markedly higher than those of the control group (see Table 3). These results indicate that the plasma G72 protein level and WBC SLC7A11 mRNA expression level can be used in combination to detect AD.

As shown in Table 4, the ROC analysis of the G72 protein levels and the $\Delta$CT values indicative of SLC7A11 mRNA expression levels in combination for the AD group vs. control group indicated an optimal cutoff value of 21.723, with good sensitivity (0.857) and modest specificity (0.675). These results suggest that the combination of the G72 protein level and the $\Delta$CT value indicative of the SLC7A11 mRNA expression level, which has a cut-off value equal to or greater than 21.723, may be indicative of AD.

In addition, it can be seen that the sensitivity of the combination of the G72 protein level and the $\Delta$CT value indicative of the SLC7A11 mRNA expression level (0.857) is greater than that of the G72 level (0.543) alone. Furthermore, the specificity of the combination of the G72 protein level and the $\Delta$CT value indicative of the SLC7A11 mRNA expression level (0.675) is greater than that of the $\Delta$CT value indicative of the SLC7A11 mRNA expression level (0.45) alone.

In particular, the combination of the G72 protein level and the $\Delta$CT value indicative of the SLC7A11 mRNA expression level (AUC=0.833) was higher in AUC than either the G72 protein level (AUC=0.726) or the $\Delta$CT value indicative of the SLC7A11 mRNA expression level (AUC=0.764) alone. Such AUC findings reveal that the combination of the G72 protein level and the SLC7A11 mRNA expression level provide for a better diagnostic ability to differentiate between the subjects in the AD and control groups than either the G72 protein level or the SLC7A11 mRNA expression level alone. Thus, there is a synergic effect when using the two biomarkers in combination when distinguishing individuals with AD from those without AD.

TABLE 3

Expression levels of Plasma G72 protein and WBC SLC7A11 mRNA in the control group and AD group

| Parameter | Control Group | AD Group | P-value |
|---|---|---|---|
| G72 level (ng/μL) | 1.72 ± 0.71 | 2.63 ± 1.20 | <0.001 |
| mRNA of SLC7A11† | 12.44 ± 1.37 | 13.82 ± 1.29 | <0.001 |
| G72 + mRNA of SLC7A11§ | 20.54 ± 4.03 | 26.59 ± 4.83 | <0.001 |

†shown as delta CT values of mRNA expressions of SLC7A11
§shown as a weighted value calculated by the equation (I)

TABLE 4

ROC Curve Analysis and Multivariate Logistic Regression of Plasma G72 Protein and/or WBC mRNA of SLC7A11 Levels of Control vs. AD groups

| | ROC curve analysis | | | |
|---|---|---|---|---|
| | Cut-off | Sensitivity | Specificity | AUC |
| G72 | >2.3285 | 54.3 | 90.0 | 0.726 |
| mRNA of SLC7A11† | >12.185 | 92.9 | 45.0 | 0.764 |
| G72 + mRNA of SLC7A11§ | >21.723 | 85.7 | 67.5 | 0.833 |

†shown as delta CT values of mRNA expressions of SLC7A11
§shown as a weighted value calculated by the equation (I)

All patents and literature references cited in the present specification as well as the references described therein, are hereby incorporated by reference in their entirety. In case of conflict, the present description, including definitions, will prevail.

While this disclosure has been described in connection with specific embodiments thereof, it will be understood that it is capable of further modifications and this application is intended to cover any variations, uses, or adaptations of the disclosure following, in general, the principles of the disclosure and including such departures from the present customary practice within the art to which the disclosure pertains and as may be applied to the essential features hereinbefore set forth, and as follows in the scope of the appended claims.

What is claimed is:

1. A method for diagnosing and treating Alzheimer's disease (AD), comprising:
   obtaining a blood sample from a human subject suspected of having AD;
   measuring a G72 protein level in the blood sample;
   measuring an SLC7A11 mRNA expression level in the blood sample;
   diagnosing the human subject with AD when the G72 protein level is higher than a first predetermined standard and the SLC7A11 mRNA expression level is higher than a second predetermined standard; and
   administering to the diagnosed human subject an effective amount of a pharmaceutical composition for treating AD.

2. The method according to claim 1, further comprising separating plasma from the blood sample, wherein the plasma is subjected to the measurement of the G72 protein level.

3. The method according to claim 2, further comprising separating white blood cells from the blood sample, wherein the white blood cells are subjected to the measurement of the SLC7A11 mRNA expression level.

4. The method according to claim 1, further comprising separating serum from the blood sample, wherein the serum is subjected to the measurement of the G72 protein level.

5. The method according to claim 1, further comprising separating white blood cells from the blood sample, wherein the white blood cells are subjected to the measurement of the SLC7A11 mRNA expression level.

6. The method according to claim 1, wherein the G72 protein level is measured using an antibody-based binding moiety which specifically binds to G72 protein.

7. The method according to claim 6, wherein the antibody-based binding moiety is labeled with a detectable label selected from the group consisting of a radioactive label, a hapten label, a fluorescent label, a chemiluminescent label, an enzymatic label and an epitope tag.

8. The method according to claim 6, wherein the G72 protein level is measured using at least one of the following methodologies: Western blot immunoassay, multiplex immunoassay, enzyme linked immunosorbent assay, radioimmunoassay, immunoradiometric assay, fluorescent immunoassay, chemiluminescent immunoassay and immunonephelometry.

9. The method according to claim 1, wherein the SLC7A11 mRNA expression level is measured using at least one of the following methodologies: polymerase chain reaction, real time polymerase chain reaction, reverse transcription polymerase chain reaction, hybridization, probe hybridization and gene expression array.

10. The method according to claim 1, wherein the pharmaceutical composition for treating AD contains an active ingredient selected from the group consisting of N-methyl-D-aspartate receptor receptor (NMDAR) antagonists, cholinesterase modulators, Aβ inhibitors, nerve growth factor agonists, hormone receptor blockade agents, neurotransmission modulators, and combinations thereof.

* * * * *